(12) United States Patent
Clodius-Talmadge

(10) Patent No.: US 7,784,466 B2
(45) Date of Patent: Aug. 31, 2010

(54) PROTECTIVE SHIELDS AND COVERS AND METHODS FOR INSTALLING THE SAME

(76) Inventor: Julie Clodius-Talmadge, P.O. Box 311, Lexington, MA (US) 02420

( * ) Notice: Subject to any disclaimer, the term of this patent is extended or adjusted under 35 U.S.C. 154(b) by 2 days.

(21) Appl. No.: 12/205,869

(22) Filed: Sep. 6, 2008

(65) Prior Publication Data
US 2009/0071485 A1 Mar. 19, 2009

Related U.S. Application Data

(63) Continuation-in-part of application No. 11/851,978, filed on Sep. 7, 2007.

(51) Int. Cl.
A61F 6/06 (2006.01)
A61F 6/14 (2006.01)
A61F 5/37 (2006.01)
A61B 19/00 (2006.01)
A61C 5/14 (2006.01)

(52) U.S. Cl. .................. 128/830; 128/841; 128/846; 128/849; 128/859

(58) Field of Classification Search ................ 128/830, 128/898, 841, 846, 849, 859; 604/385.05
See application file for complete search history.

(56) References Cited

U.S. PATENT DOCUMENTS

| | | |
|---|---|---|
| D31,271 S | 7/1899 | Halleck |
| 1,517,166 A | 11/1924 | Powers |
| 1,907,063 A | 5/1933 | Golanke |
| 3,176,686 A | 4/1965 | Barnes |
| 3,339,208 A | 9/1967 | Marbach |
| 3,782,375 A | 1/1974 | Donars |
| 4,449,980 A * | 5/1984 | Millar et al. ............. 424/430 |
| 4,942,891 A | 7/1990 | Trevisan |
| 4,977,672 A | 12/1990 | Hamilton |
| 4,982,450 A | 1/1991 | D'Huissier |
| 5,174,307 A | 12/1992 | Thompson |
| 5,207,233 A | 5/1993 | Barnes |
| 5,450,671 A | 9/1995 | Harshman |
| D364,262 S | 11/1995 | Magidson et al. |
| 5,467,482 A | 11/1995 | Crawford, II |
| 5,483,705 A | 1/1996 | DiMatteo |
| 5,669,395 A | 9/1997 | Thompson |
| D395,735 S | 7/1998 | Paramore |
| 5,827,302 A | 10/1998 | Kandarian et al. |
| 5,832,535 A | 11/1998 | Davis |
| 5,842,474 A | 12/1998 | Blyskal et al. |
| 5,884,340 A | 3/1999 | Chen et al. |
| 6,319,219 B1 | 11/2001 | Landi |
| 6,336,462 B1 | 1/2002 | Santelli et al. |
| 6,655,389 B2 | 12/2003 | Bertucci |
| 6,681,771 B2 * | 1/2004 | Durette ............. 128/859 |
| 7,051,379 B2 | 5/2006 | Lambert |

(Continued)

FOREIGN PATENT DOCUMENTS

WO WO2005/002387 5/2005

*Primary Examiner*—Patricia M Bianco
*Assistant Examiner*—Ophelia Hawthorne

(57) ABSTRACT

Protective shields with and without retaining wings and shield cover for protecting the vulva and labia minora of a female. The protective shield is shaped to conform to the outer shape of the labia minora and may include retaining wings which hold the shield in place. An outer cover may be installed on the shield for protective and ornamental purposes.

17 Claims, 8 Drawing Sheets

U.S. PATENT DOCUMENTS

| | | |
|---|---|---|
| 7,296,307 B2 * | 11/2007 | Atwater et al. ............. 2/466 |
| 2002/0183707 A1 * | 12/2002 | Schmitt ............. 604/385.04 |
| 2004/0158221 A1 | 8/2004 | Mizutani et al. |
| 2005/0000536 A1 | 1/2005 | Notorio |
| 2005/0205105 A1 | 9/2005 | Demko |
| 2006/0254608 A1 | 11/2006 | Lam |
| 2007/0244352 A1 * | 10/2007 | Ziv ............................. 600/29 |
| 2008/0142020 A1 | 6/2008 | Chapin |

* cited by examiner

US 7,784,466 B2

PROTECTIVE SHIELDS AND COVERS AND METHODS FOR INSTALLING THE SAME

PRIORITY INFORMATION

This application is a continuation-in-part of U.S. patent application Ser. No. 11/851,978 entitled "Protective Shield and Cover" filed on Sep. 7, 2007, and is hereby incorporated by reference for all that it teaches.

BACKGROUND OF INVENTION

The present invention pertains generally to hair removal products, and more particularly to protective shields and cover for protecting the vulva and labia minora of a female.

Hair removal of hair from genital areas is often performed for cosmetic or medical reasons. For example, it may be necessary to shave the pubic area prior to surgery or other medical procedures. As further example it may be deemed aesthetically desirable to remove hair from the pubic region, as in the case of the recently popular bikini and brazilian-style waxing procedures.

As the demand for bikini hair removal procedures increases, so does the demand for related products. There are many methods for removing unwanted pubic hair, including waxing, shaving, using a depilatory, and laser hair removal. Waxing, such as the "brazilian wax", is a currently popular choice, and is offered at many beauty salons and spas. Laser removal is becoming increasingly popular due to its success with permanently removing unwanted hair. Hair removal in a female's pubic region typically requires full exposure of the vulva area to ensure complete hair removal, placing the sensitive regions of the female genitalia at risk for damage and pain.

SUMMARY OF INVENTION

Embodiments of the invention include a protective shield comprising a main body shaped and adapted to be positioned so as to cover the labia minora and vulva of the female, the main body having a cap and two opposing lateral sides extending from the cap to form a recess, the main body positionable over the labia minora of the female with the lateral sides fitting between the labia minora and labia majora of the female such that the vulva and labia minora are covered by the main body and held in place using the natural contours of the labia minora.

Embodiments of the invention include a protective shield comprising a main body shaped and adapted to be positioned so as to cover the labia minora and vulva of the female, the main body having a cap with two opposing lateral sides extending therefrom to form a cavity or recess. The outer surface of the main body includes at least one pair of outwardly projecting retaining wings. To install the protective shield in protective position, the shield is positioned over the labia minora of the female such that the lateral sides are inserted between the labia minora and labia majora of the female and the retaining wings hold the such that the vulva and labia minora are covered by the main body and held in place only by the natural contours of the labia minora.

Embodiments of the invention may also include an outer cover for placement over the main body of the protective shield, wherein the outer cover includes an inner cavity that substantially conforms to an outer surface of the main body. The outer cover may be used for both protective purposes and ornamentation.

Embodiments of the invention may also include a method for protecting a vulva and labia minora of a human female, the method comprising installing a protective shield over the labia minora of a the female, the protective shield comprising a main body shaped and adapted to be positioned so as to cover the labia minora and vulva of the female, the main body having a cap and two opposing lateral sides extending from the cap to form a recess, the main body positionable over the labia minora of the female with the lateral sides fitting between the labia minor and labia major of the female such that the vulva and labia minora are covered by the main body and held in place only by the natural contours of the labia minora.

Embodiments of the invention may also include a method for protecting a vulva and labia minora of a human female, the method comprising installing a protective shield over the labia minora of a the female, the protective shield comprising a main body shaped and adapted to be positioned so as to cover the labia minora and vulva of the female, the main body having a cap and two opposing lateral sides extending from the cap to form a recess, the lateral sides having one or more retaining wings projecting outwardly therefrom, the main body positionable over the labia minora of the female with the lateral sides contacting the labia minora of the female and the one or more retaining wings contacting the labia majora of the female such that the vulva and labia minora are covered by the main body and held in place by the forces of the labia majora against the one or more retaining wings.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

Figure 1:
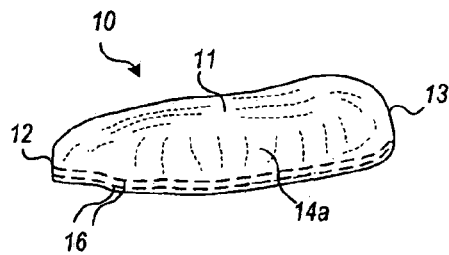
FIG. 1 is a perspective view of an exemplary embodiment of a protective shield.
Figure 2:
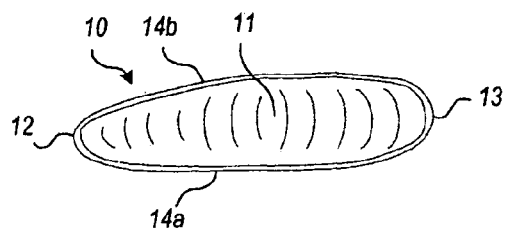
FIG. 2 is a top view of the protective shield of FIG. 1.
Figure 3:
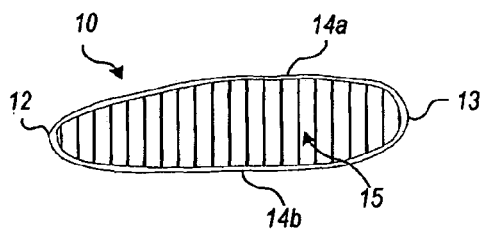
FIG. 3 is a bottom view of the protective shield of FIG. 1.
Figure 4:
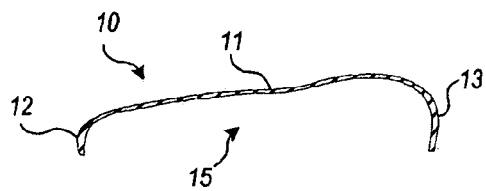
FIG. 4 is a lengthwise cross-sectional view of the protective shield of FIG. 1.
Figure 5:
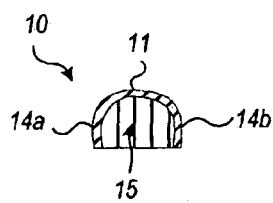
FIG. 5 is a crosswise cross-sectional view of the protective shield of FIG. 1.
Figure 6:
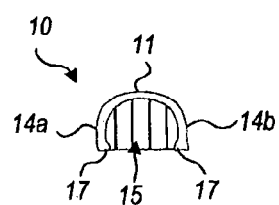
FIG. 6 is a crosswise cross-sectional view of the protective shield of FIG. 1 having interior retaining ridges.
Figure 7:
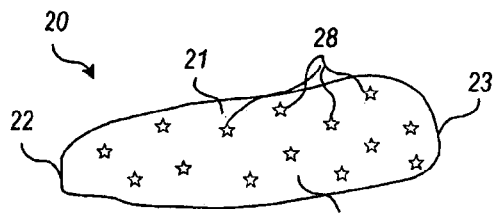
FIG. 7 is a perspective view of an exemplary embodiment of an outer cover for a protective shield implemented in accordance with one of FIGS. 1 and 28.
Figure 8:
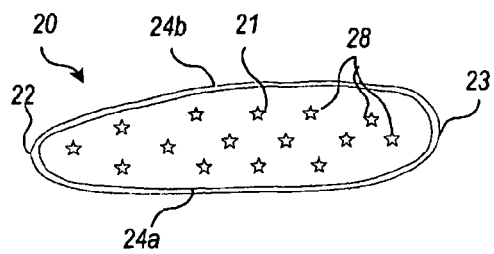
FIG. 8 is a top view of the outer cover of FIG. 7.
Figure 9:
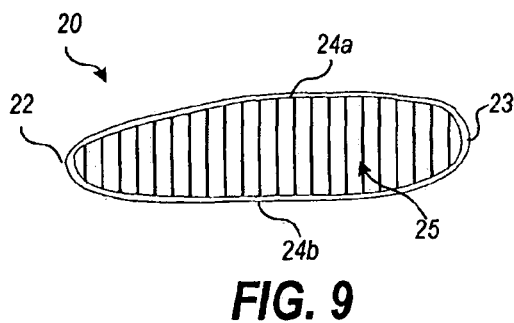
FIG. 9 is a bottom view of the outer cover of FIG. 7.
Figure 10:
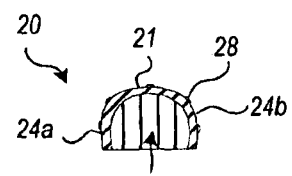
FIG. 10 is a crosswise cross-sectional view of the outer cover of FIG. 7.
Figure 11:
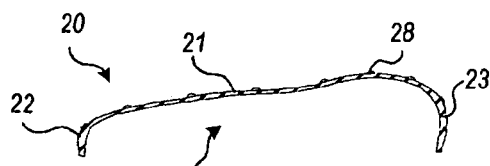
FIG. 11 is a lengthwise cross-sectional view of the outer cover of FIG. 7.
Figure 12:
FIG. 12 is a perspective view illustrating the installation of the outer cover of FIG. 7 over the protective shield of FIG. 1.
Figure 13:
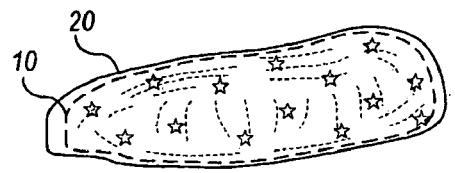
FIG. 13 is a perspective view of the outer cover of FIG. 7 installed over the protective shield of FIG. 1.
Figure 14:
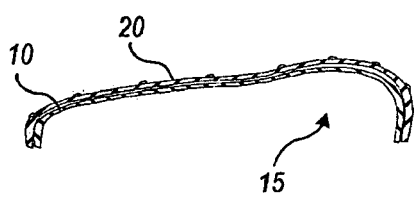
FIG. 14 is a lengthwise cross-sectional view of the outer cover of FIG. 7 installed over the protective shield of FIG. 1.

Embodiments of the invention include protective shields and methods of use thereof for removal of hair in the female genital area. Such techniques may include, but are not limited to, waxing, laser removal, electrolysis removal, shaving, and use of depilatory creams, gels or sprays.

Referring now to a first embodiment illustrated in FIGS. 1-20, there is shown a protective shield 10 for use in protecting the female genital area, i.e., the vulva 36 and the delicate membrane of the vaginal and urethral openings, the labia minora 34 and all other very sensitive features. The protective shield 10 is generally shaped to fit over the entire labia minora 34 of a human female, and is designed to fit between the labia minora 34 and the labia majora 32 with the protective shield 10 positioned around and over, and held in place by, the labia minora 34.

As best shown in FIGS. 1-5, the protective shield 10 is generally formed of a main body integrally comprising a cap 11 and two opposing lateral sides 14a, 14b extending from the cap 11 and joined together at opposing ends 12, 13 of the cap 11 to form a cavity 15 which substantially conforms to the shape of the labia minora 34.

Figure 18:
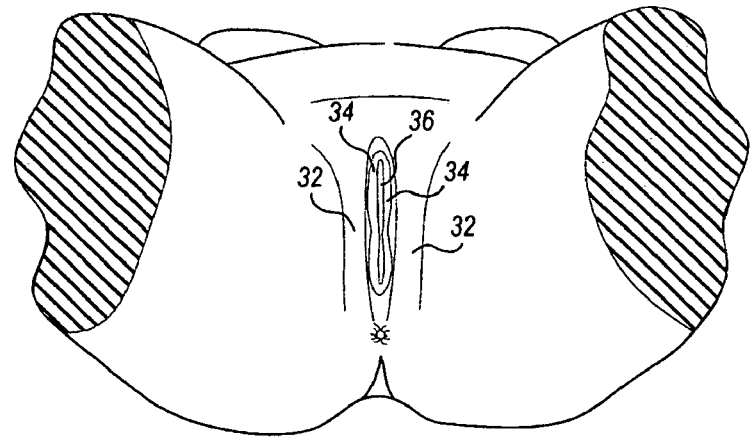
FIG. 18 is a view of the perineum of the human female.
Figure 19:
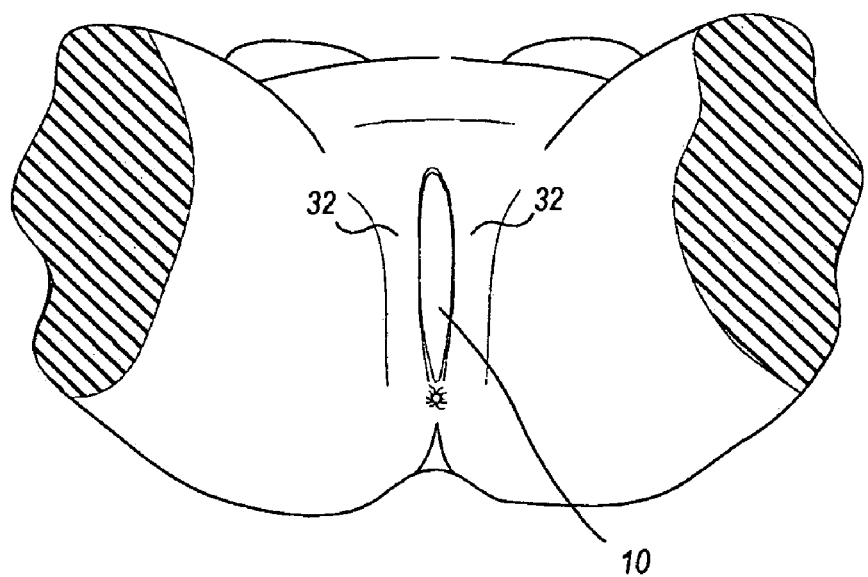
FIG. 19 is a view of the perineum of the human female with a protective shield installed.
Figure 20:
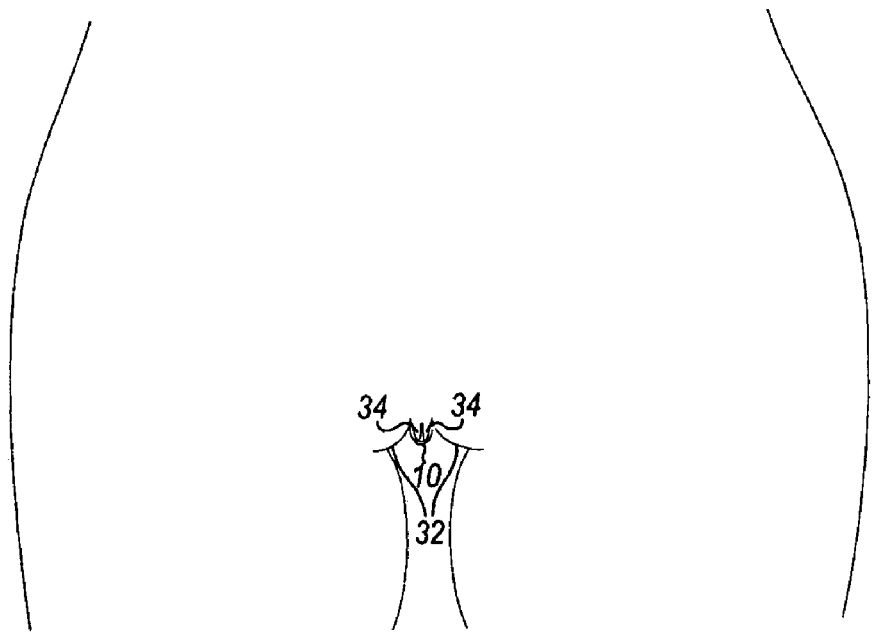
FIG. 20 is a front cross-sectional view of the perineum of the human female with the protective shield of the embodiment of FIG. 1 installed.
Figure 21:
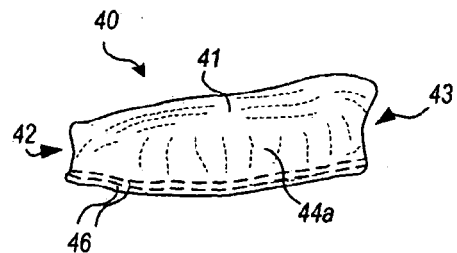
FIG. 21 is a perspective view of an alternative embodiment of a protective shield.
Figure 22:
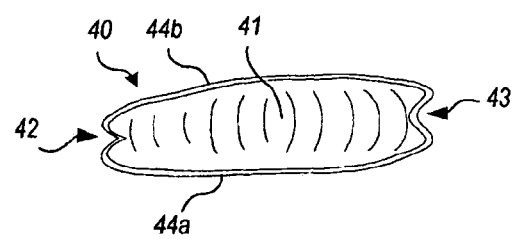
FIG. 22 is a top view of the protective shield of FIG. 21.
Figure 23:
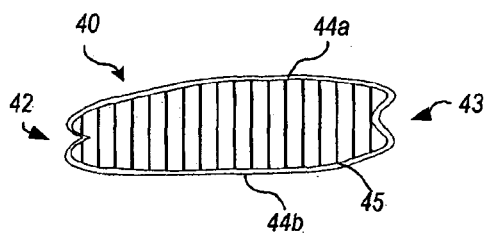
FIG. 23 is a bottom view of the protective shield of FIG. 21.
Figure 24:
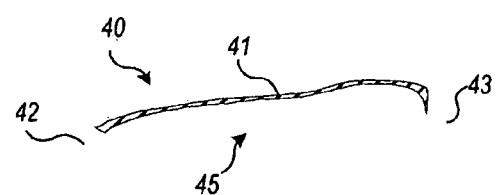
FIG. 24 is a lengthwise cross-sectional view of the protective shield of FIG. 21.
Figure 25:
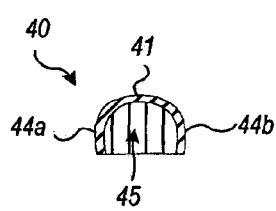
FIG. 25 is a crosswise cross-sectional view of the protective shield of FIG. 21.
Figure 26:
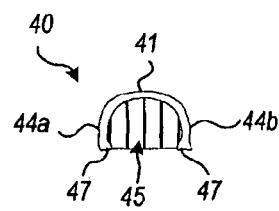
FIG. 26 is a crosswise cross-sectional view of the protective shield of FIG. 21 having interior retaining ridges.
Figure 27:
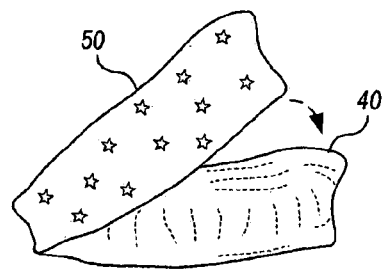
FIG. 27 is a perspective view illustrating the installation of an alternative embodiment of an outer cover over the protective shield of FIG. 21.
Figure 28:
FIG. 28 is a perspective view of the alternative embodiment of the outer cover of FIG. 27 installed over the protective shield of FIG. 21.
Figure 29:
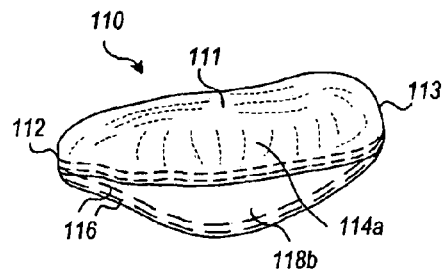
FIG. 29 is a perspective view of an alternative embodiment of a protective shield.
Figure 30:
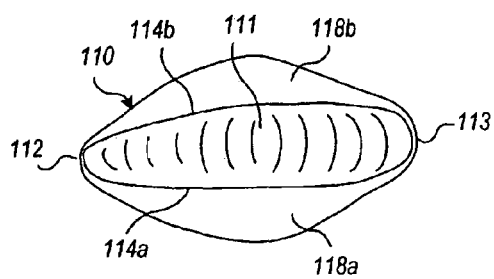
FIG. 30 is a top view of the protective shield of FIG. 28.
Figure 31:
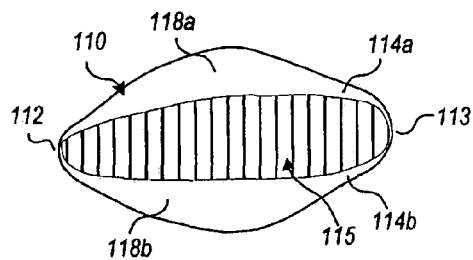
FIG. 31 is a bottom view of the protective shield of FIG. 28.
Figure 32:
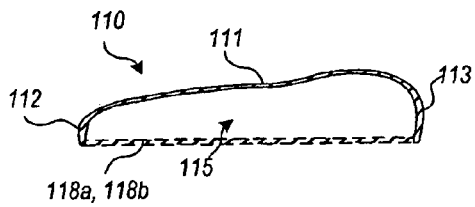
FIG. 32 is a lengthwise cross-sectional view of the protective shield of FIG. 28.
Figure 33:
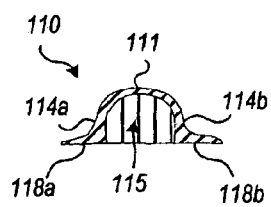
FIG. 33 is a crosswise cross-sectional view of the protective shield of FIG. 28.

During use, as illustrated in FIGS. 18-20, the protective shield 10 is positioned over the labia minora 34 of the female with the lateral sides 14a, 14b, fitting between the labia minora 34 and labia majora 32 of the female such that the vulva 36 and labia minora 34 are covered by the cap 11, and such that the labia minora 34 fits within the cavity 15 of the protective shield 10. The protective shield 10 is self-held in place by the natural contours of the labia minora 34. In an embodiment, illustrated in FIG. 6, the outer edges of the lateral sides are configured with a ridge formation 17 which provide additional gripping action.

In an embodiment, the protective shield 10 is formed of a soft rubbery polymer material, which naturally grips the labia minora 34 of the user, and due to its non-breathable characteristics, may be installed over the labia minora 34 so as to form a vacuum, which further assists in holding the protective shield 10 in place when positioned in place over the labia minora 34 via suction action. The soft rubbery polymer material may be, by way of illustration only and not limitation, an elastomer or ethylene-vinyl acetate (EVA). The material may also be silicon, which disperses and reflects light energy so as to prevent penetration of light energy completely through the material when used for laser hair removal. The material may also be made of other materials, such as rubber, plastic, vinyl, etc. In an embodiment, the color of the protective shield 10 is a color that substantially disperses and reflects, or blocks, light energy so as to prevent penetration of the light energy through the shield.

The cavity 15 of the protective shield 10 is formed to accommodate labia minora 34 of different sizes and shapes that may exist because of the difference between the anatomies of females, especially on the upper aspect of the genital area, where some patients have a larger clitoris or labia minora 34. As stated above, the protective shields 10 of the embodiments of the invention are made of a soft rubbery polymer to provide for a better and more comfortable fit regardless of the individual features of the patient. With this shape and construction, the protective shield 10 will fit most patients so that the user's entire labia minora 34 is covered. Preferably, the inner and outer surfaces of the main body are customized to the anatomy of the user's labia minora and labia majora. To accommodate different sizes of labia minora 34, the protective shield 10 may be made in different sizes. Alternatively, the main body of the protective shield 10 may be formed with indicator lines along the edges of the lateral sides of the main body to guide a user or practitioner in decreasing the depth of the cavity of the protective shield 10. In other words, the user or practitioner may use the indicator lines 16 to cut the protective shield 10, for example using scissors, down to size to snugly accommodate the labia minora of the user yet so as to allow as little air as possible in the cavity 15 when installed over the labia minor of the user.

Figure 15:
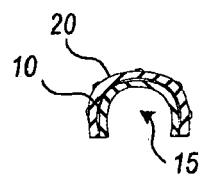
FIG. 15 is a crosswise cross-sectional view of the outer cover of FIG. 7 installed over the protective shield of FIG. 1.
Figure 16:
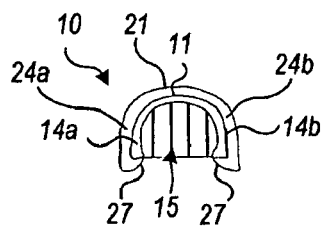
FIG. 16 is a crosswise cross-sectional view of the outer cover of FIG. 7 installed over the protective shield of FIG. 6.
Figure 17:
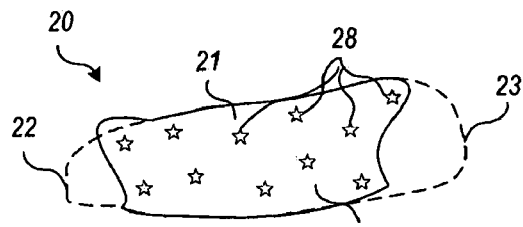
FIG. 17 is a perspective view of an alternative embodiment of an outer cover installed over the protective shield of FIG. 1.

In an embodiment, illustrated in FIGS. 12-17, the protective shield 10 includes an outer cover 20 which may be used to prevent penetration of light energy to the shield, and/or for ornamentation. In one embodiment, the outer cover 20 is removable from the protective shield 10, as shown removed from the shield 10 in FIGS. 7-11. In another embodiment, the outer cover 20 is non-removable from the protective shield 10. The outer surface of the outer cover 20 may be of any shape, for example conforming to the shape of the protective shield as shown in FIGS. 12-15, or of any other shape, for example as shown in FIG. 17. However, the inner surface of the outer cover 20 forms a cavity 25 (see FIGS. 9 and 11)

which substantially conforms to an outer surface of at least a portion of the main body of the protective shield 10 over which the outer cover 20 is configured to be positioned. The protective shield 10 may include means for retaining the protective shield 10 within the cavity when placed over the protective shield 10. In an embodiment, the retaining means is the implementation of the protective shield 10 with a soft polymer material that naturally grips the inner surface of the protective shield 10 through friction, as illustrated in FIG. 15. In another embodiment, the retaining means is an inward-formed ridge 27 as shown in FIG. 16. Other retaining means may include mating grooves or ridges, clips, snaps, etc.

In an embodiment, the outer cover 20 is made of a material which blocks, disperses, and/or reflects light energy.

In an embodiment, the outer cover 20 is made of a metal such as, but not limited to, silver, platinum, or gold.

In an embodiment, the outer cover 20 includes ornamentation such as, but not limited to, embedded jewels 28 or precious stones, engravings, and enamels.

The installation of the protective shield 10 (with or without the outer cover 20) can be performed by the user herself or a hair removal practitioner. The presence of the protective shield 10 between the labia minora 34 and the labia majora 32 enables the practitioner to stretch the labia majora 32 in order to expose the hair that is to be removed by lasing the hair follicles without exposing the female's entire vulvic area.

As described above, the protective shield 10 is specifically contoured to fit over the woman's labia minora 34 and held in place by custom fit inside the labia majora 32. When installed over the labia minora 34 to remove as much air as possible, the protective shield 10 may also stay in place due to suction action. This design allows the user or practitioner to stretch the labia majora 32, as is performed in waxing procedures, for example, in order to expose all hair for removal while protecting the more sensitive areas of the user's vulva regions which are covered by the shield 10.

In an embodiment, the thickness the outer cover 20 is approximately 0.5 mm-1 mm, depending on the material used to form the outer cover 20. The soft inner protective shield 10 is generally 2 mm-3 mm thick. In an embodiment, the shield 10 is approximately 1.5 cm in width, 7.5 cm in length, and 1.5 cm-2 cm in height before trimmed to custom fit. Although one size may be made to accommodate most women, it may be desirable to make each protective shield 10 in more than one size or to provide one size with indicator lines 16 that allow an individual user to trim the size specific to the user. Of course, the measurements provided herein are only for purposes of example and not limitation, and it is to be understood that different thicknesses may be utilized for different applications and that a shield 10 may even have regions of varying thickness.

FIGS. 21-28 illustrate an alternative embodiment of a protective shield 40 and cover 50. In this embodiment, the main body of the shield 40 comprises a cap 41 and two opposing lateral sides 44a, 44b extending from the cap 41. In this embodiment, one or both of the opposing ends of the elongate cap are left open. That is, the two opposing lateral sides 44a, 44b are not joined together at opposing ends 42, 43 of the cap 41. Nonetheless, the inner surfaces of the elongate cap 41 and opposing lateral sides 44a, 44b form a recess 45a which accommodates, and preferably substantially conforms to the outer shape of, the user's labia minora 34. In all other respects, the embodiment shown in FIGS. 21-28 is formed and operates similarly to that described with respect to the embodiment of FIGS. 1-20.

Referring now to another alternative embodiment illustrated in FIGS. 29-36, there is shown a protective shield with retaining wings 110. The protective shield 110 of FIGS. 21-36 is generally shaped to fit over the entire labia minora 34 of a human female, and is designed with retaining wings 118 which fit between the labia minora 34 and the labia majora 32 to hold the protective shield 110 in place using the natural anatomical features of the labia majora.

As best shown in FIGS. 29-34, the protective shield 110 is generally formed of a main body integrally comprising a cap 111 and two opposing lateral sides 114a, 114b extending from the cap 111. In one embodiment, the lateral sides 114a, 114b are joined together at opposing ends 112, 113 of the elongate cap 111 to form a cavity 115, per the embodiment shown in FIGS. 1-20. In another embodiment, the lateral sides 114a, 114b are not joined at one or both of the opposing ends 112, 113, per the embodiment shown in FIGS. 21-28. In either embodiment, the protective shield comprises at least one pair of outwardly projecting retaining wings 118a, 118b on the outer surface of the main body. In the embodiments shown in FIGS. 29-34, the retaining wings are attached to, and are preferably integral to, the lateral sides 114a, 114b of the main body 111. The retaining wings 118a, 118b are relatively stiff so as not to collapse when inserted in place between the labia minora 34 and labia majora 32 of the user. Thus, while in one embodiment the retaining wings are manufactured using a rubbery polymer, the material is characterized nonetheless by a relatively high stiffness quotient in order that it does not lose its natural shape during use. In an embodiment, the retaining wings 118a, 118b may be configured with a higher stiffness quotient than the main body 111.

Figure 34:
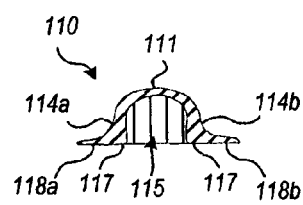
FIG. 34 is a crosswise cross-sectional view of the protective shield of FIG. 28 having interior retaining ridges.
Figure 35:
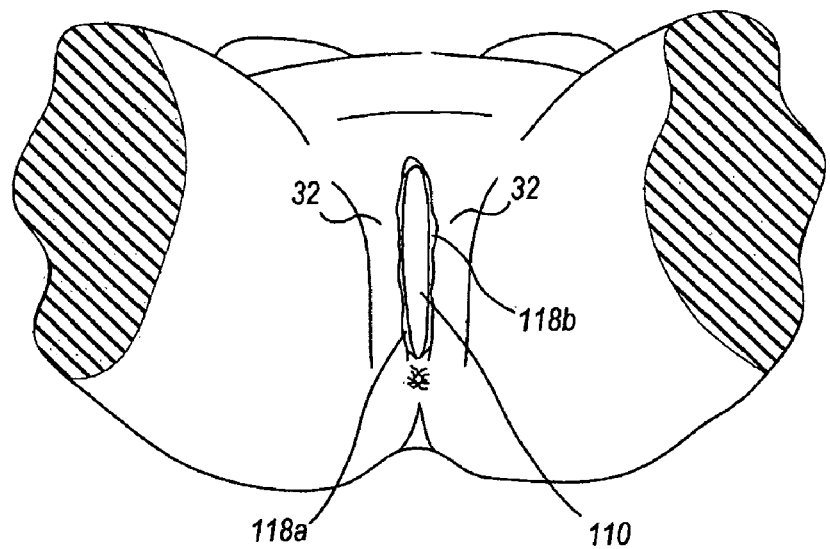
FIG. 35 is a view of the perineum of the human female with the protective shield of the embodiment of FIGS. 29-34 installed.
Figure 36:
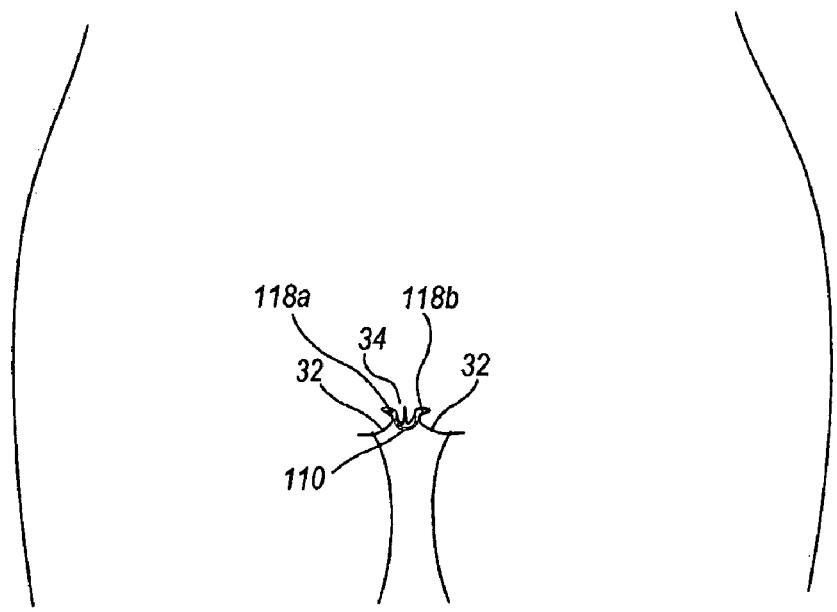
FIG. 36 is a front cross-sectional view of the perineum of the human female with the protective shield of the embodiment of FIGS. 29-34 installed.

During use, as illustrated in FIGS. 35-36, the protective shield 110 is positioned over the labia minora 34 of the female such that the labia minora 34 fits snugly within the cavity 115 or recess 115a and the vulva 36 and labia minora 34 are covered by the cap 111 and lateral sides 114a, 114b. The recess 115 formed by the cap 111 and lateral sides 114a, 114b is designed to accommodate the entire labia minora 34 of a female user yet leave as little room as possible for excess air. Removing as much air as possible from the recess 115 during installation of the shield 110 over the labia minora 34 of the user increases the natural grip of the shield 110 over the labia minora 34. The lateral sides 114a, 114b with retention wings 118a, 118b are inserted between the labia minora 34 and labia majora 32 of the female user, and the force asserted against the retention wings 118a, 118b by the labia majora 32 assists in holding the protective shield 110 in place. Retention wings 118a, 118b which project laterally from the lateral sides 114a, 114b of the main body of the protective shield 110, hold the protective shield 110 in place against the labia majora 32, utilizing frictional force between the retaining wings 118a, 118b and the natural contours of the labia majora 32. Optionally, as illustrated in FIG. 34, the inner surfaces of the lateral sides 114a, 114b are configured with a ridge formation 117 which provide additional retention force against the labia minora 34 of the female user.

In an embodiment, the protective shield 110 is formed of a soft rubbery polymer material, which naturally grips the labia minora 34 of the user, and due to its non-breathable characteristics, may be installed over the labia minora 34 so as to form a vacuum, which further assists in holding the protective shield 110 in place when positioned in place over the labia minora 34 via suction action. The soft rubbery polymer material may be, by way of illustration only and not limitation, an elastomer or ethylene-vinyl acetate (EVA). The material may also be silicon, which disperses and reflects light energy so as to prevent penetration of light energy completely through the material when used for laser hair removal. The material may also be made of other materials, such as rubber, plastic, vinyl, etc. In an embodiment, the color of the protective shield 110 is a color that substantially disperses and reflects, or blocks, light energy so as to prevent penetration of the light energy through the shield.

The cavity 115 of the protective shield 110 is formed to accommodate labia minora 34 of different sizes and shapes that may exist because of the difference between the anatomies of females, especially on the upper aspect of the genital area, where some patients have a larger clitoris or labia minora 34. As stated above, the protective shields 10 of the embodiments of the invention are made of a soft rubbery polymer to provide for a better and more comfortable fit regardless of the individual features of the patient. With this shape and construction, the protective shield 10 will fit most patients so that the user's entire labia minora 34 is covered. To accommodate different sizes of labia minora 34, the protective shield 10 may be made in different sizes. Alternatively, the retaining wings 118a, 118b of the protective shield 110 may be formed with indicator lines 116 along the outer edges of the retaining wings 118a, 118b to guide a user or practitioner in decreasing the width of the retaining wings 118a, 118b. In other words, the user or practitioner may use the indicator lines 116 to trim the width of the retaining wings 118a, 118b to custom fit the user.

In an embodiment, the protective shield 110 includes an outer cover 20, for example as previously described with respect to FIGS. 7-17, which may be installed over the shield 110 and used to prevent penetration of light energy to the shield, and/or for ornamentation. In one embodiment, the outer cover 20 is removable from the protective shield 110. In another embodiment, the outer cover 20 is non-removable from the protective shield 110. The outer surface of the outer cover 20 may be of any shape, for example conforming to the shape of the protective shield 110 as shown in FIGS. 29-34, or of any other shape, for example including coverage of the retaining wings 118a, 118b. However, the inner surface of the outer cover 20 forms a cavity 25 which substantially conforms to an outer surface of at least a portion of the main body of the protective shield 110 over which the outer cover 20 is configured to be positioned. The protective shield 110 may include means for retaining the protective shield 110 within the cavity when placed over the protective shield 110. In an embodiment, the retaining means is the implementation of the protective shield 110 with a soft polymer material that naturally grips the inner surface of the protective shield 110 through friction. Other retaining means may include an inward-formed ridge 27, mating grooves or ridges, clips, snaps, etc.

In an embodiment, the outer cover 20 is made of a material which blocks, disperses, and/or reflects light energy.

In one embodiment, the outer cover 20 is made of a metal such as, but not limited to, silver, platinum, or gold.

In one embodiment, the outer cover 20 includes ornamentation such as, but not limited to, embedded jewels 28 or precious stones, engravings, and enamels.

The installation of the protective shield 110 (with or without the outer cover 20) can be performed by the user herself or a hair removal practitioner. The presence of the protective shield 10 between the labia minora 34 and the labia majora 32 enables the practitioner to stretch the labia majora 32 in order to expose the hair that is to be removed.

The unique fitted design of a protective shield 110 with or without the outer cover 20 is suited for placement by the user for home use or to wear to a hair removal practitioner's office or salon for personal cover. Although described herein with respect to use in hair removal procedures, the protective shield 110 with or without the outer cover 20 is also ideal for use in nude sunbathing and in surgical procedures performed near the sensitive vulva area.

Figure 37:
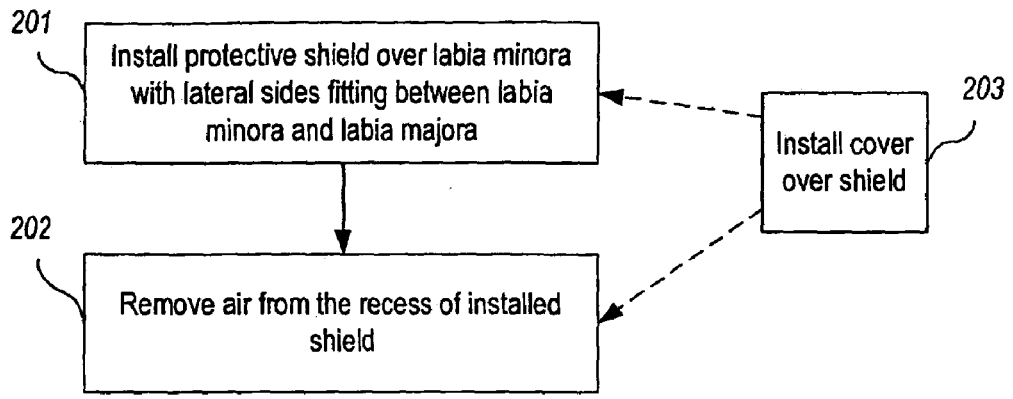
FIG. 37 is a flowchart of an exemplary embodiment of a method for protecting a vulva and labia minora of a human female.

FIG. 37 is a flowchart illustrating an exemplary method for protecting a vulva and labia minora of a human female. The method 200 includes the steps of installing a protective shield over the labia minora of a the female, the protective shield comprising a main body shaped and adapted to be positioned so as to cover the labia minora and vulva of the female, the main body having a cap and two opposing lateral sides extending from the cap to form a recess, the main body positionable over the labia minora of the female with the lateral sides fitting between the labia minor and labia major of the female such that the vulva and labia minora are covered by the main body (step 201); and removing as much air as possible from the recess, for example by squeezing the main body to push any air out of the recess (step 202). The result is that the protective shield may be held in place only by the natural contours of the labia minora.

In an embodiment, the method may further comprise installing an outer cover over the protective shield before or after installing the protective shield over the labia minora of the female (step 203).

Figure 38:
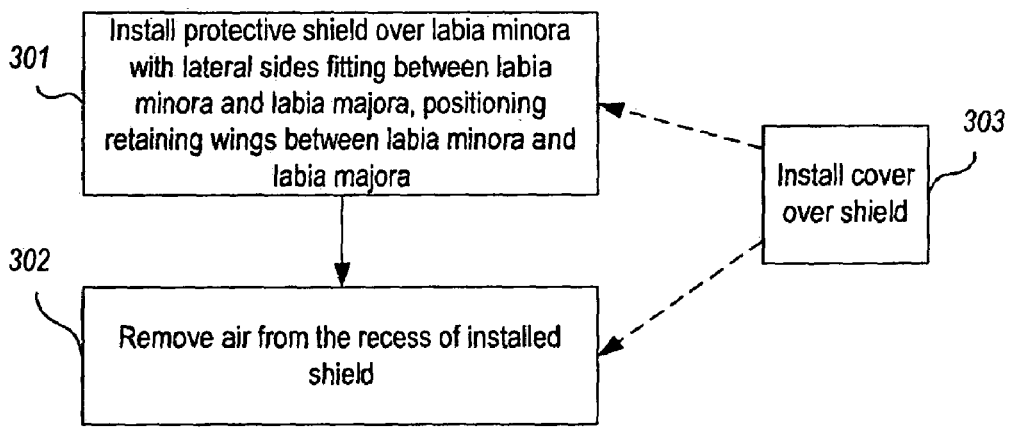
FIG. 38 is a flowchart of an exemplary embodiment of a method for protecting a vulva and labia minora of a human female.

FIG. 38 is a flowchart illustrating an exemplary method for protecting a vulva and labia minora of a human female. The method 200 includes the steps of installing a protective shield over the labia minora of a the female, the protective shield comprising a main body shaped and adapted to be positioned so as to cover the labia minora and vulva of the female, the main body having a cap and two opposing lateral sides extending from the cap to form a recess, the lateral sides having one or more retaining wings projecting outwardly therefrom, positioning the main body over the labia minora of the female with the lateral sides contacting the labia minora of the female and the one or more retaining wings contacting the labia majora of the female such that the vulva and labia minora are covered by the main body and held in place by the forces of the labia majora against the one or more retaining wings (step 301); removing as much air as possible from the recess, for example by squeezing the main body to push any air out of the recess (step 302); and. The result is that the protective shield may be held in place by the natural contours of the labia minora via the gripping action of the main body and the frictional forces of the labia against the retaining wings.

In an embodiment, the method may further comprise installing an outer cover over the protective shield before or after installing the protective shield over the labia minora of the female (step 303).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A protective shield, said protective shield comprising:
a cap, two opposing lateral sides extending from the cap to form a recess which substantially conforms to an outer shape of the labia minora of the female, and one or more retaining wings projecting outward from the lateral sides, wherein the two opposing lateral sides are configured to naturally grip the labia minora and the one or more retaining wings are configured to maintain their outward projecting shape when the protective shield is installed over the labia minora of a female with the two opposing lateral sides and one or more retaining wings fitting between the labia minora and labia majora of the female and such that the lateral sides are held in place by the labia minora of the female and the retaining wings are held in place by the labia majora of the female.

2. The protective shield of claim 1, wherein the two lateral sides are joined at a first end of the cap.

3. The protective shield of claim 2, wherein the two lateral sides are joined at a second end of the cap opposite the first end of the cap.

4. The protective shield of claim 1 formed of a soft polymer material.

5. The protective shield of claim 1 formed of an ethylene vinyl acetate material.

6. The protective shield of claim 1, wherein an inner surface of the recess comprises one or more ridge formations configured to provide retention force against the labia minora when the protective shield is installed over the labia minora of the female.

7. The protective shield of claim 1 made of a color that disperses, reflects, or blocks light energy so as to prevent penetration of the light energy completely through the material.

8. The protective shield of claim 1 further comprising indicator lines along the edges of the lateral sides for use as guides in decreasing the depth of the cavity of the protective shield.

9. The protective shield of claim 1, comprising an outer cover having an inner cavity that substantially conforms to an outer surface of at least a portion of the protective shield over which the outer cover is configured to be positioned.

10. The protective shield of claim 9, wherein the outer cover comprises a metal material.

11. The protective shield of claim 9, wherein the outer cover comprises ornamentation.

12. The protective shield of claim 9, wherein the outer cover comprises retaining means for retaining the protective shield.

13. The protective shield of claim 9, wherein the outer cover is removable from the protective shield.

14. The protective shield of claim 9, wherein the outer cover is permanently attached to the protective shield.

15. The protective shield of claim 1, wherein the one or more retaining wings are configured with indicator lines along the outer edges of the retaining wings for use as guides in decreasing the width of the retaining wings.

16. A method for protecting a vulva and labia minora of a human female, the method comprising:
    installing a protective shield over the labia minora of a the female, the protective shield comprising a cap, two opposing lateral sides extending from the cap to form a recess which substantially conforms to an outer shape of the labia minora of the female, and one or more retaining wings projecting outward from the lateral sides, the installing comprising positioning the two opposing lateral sides and one or more retaining wings between the labia minora and labia majora of the female and such that the lateral sides are held in place by the labia minora of the female and the retaining wings are held in place by the labia majora of the female;
    wherein the two opposing lateral sides are configured to naturally grip the labia minora and the one or more retaining wings are configured to maintain their outward projecting shape when the protective shield is installed.

17. The method of claim 16, comprising:
    installing an outer cover over the protective shield before or after installing the protective shield over the labia minora of the female.

* * * * *